(12) United States Patent
Tontarra

(10) Patent No.: US 6,802,852 B2
(45) Date of Patent: Oct. 12, 2004

(54) SURGICAL INSTRUMENT

(75) Inventor: Thomas Tontarra, Wurmlingen (DE)

(73) Assignee: Tontarra Medizintechnik GmbH, Wurmlingen (DE)

(*) Notice: Subject to any disclaimer, the term of this patent is extended or adjusted under 35 U.S.C. 154(b) by 106 days.

(21) Appl. No.: 10/016,372

(22) Filed: Dec. 9, 2001

(65) Prior Publication Data
US 2002/0151931 A1 Oct. 17, 2002

(30) Foreign Application Priority Data
Dec. 8, 2000 (DE) .......................................... 100 61 512

(51) Int. Cl.$^7$ ............................................. A61B 17/28
(52) U.S. Cl. ....................................................... 606/208
(58) Field of Search ................................. 606/167, 170, 606/174, 205, 207, 208, 210

(56) References Cited

U.S. PATENT DOCUMENTS 5,582,618 A * 12/1996 Chin et al. .................. 606/170
6,126,674 A * 10/2000 Janzen ........................ 606/208

* cited by examiner

Primary Examiner—Kevin T. Truong

(57) ABSTRACT

The invention relates to a surgical instrument with a main part and at least one movable part movable relative thereto, with a handle arranged on the main part and having a stationary handle portion and a handle portion which can actuate the movable part. A locking device is provided in which, in a first position, the movable part is arranged in an initial position, and in a second position, the movable part can be changed over into a cleaning position and the movable part in this position is arranged captive with respect to the main part.

34 Claims, 10 Drawing Sheets

SURGICAL INSTRUMENT

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention relates to a surgical instrument having a main part and at least one part movable relative thereto and also a handle which has a stationary handle portion connected to the main part and an actuatable handle portion connected to the movable part.

TECHNICAL FIELD

Such surgical instruments are known, for example, through the Janit company. With these surgical instruments, punches are concerned which are used to remove tissue, bone or the like in surgical operations. These devices have a main part and at least one part movable relative thereto, a so-called slider, and also a handle which has a stationary handle portion connected to the main part and an actuatable handle portion connected to the movable part. The movable part is closed and opened relative to the main part by opening and closing the handle portion, and the removal of tissue, bone or the like, for example, is made possible during the closing movement.

Such surgical instruments have to be cleaned and sterilized after each surgical operation, in order to prevent the transmission of infections or the like in further operations. However, these instruments have the disadvantage that the movable part is not releasable from the main part, so that bacteria can collect in the region of guides between the movable part and the main part.

A surgical instrument is known from DE 4316768 A1, in which the movable part can be completely released and removed from the main part for cleaning and sterilization. The main part and the movable part are there provided with respective identifications, so that after the cleaning and sterilization of the instruments an allocation of the movable part to the main part is made possible. This is required, since surgical instruments are finished by grinding in the assembled state, in order to make possible a transition which is free from shoulders between the main part and the movable part. Such instruments have the disadvantage that the handle likewise has to be at least partially released from the main part and the movable part has to be at least partially removed from the main part. The coordination of the paths of movement of several components for assembly is thereby also made difficult.

SUMMARY OF THE INVENTION

The invention therefore has as its object to provide a surgical instrument which for cleaning and sterilization can be at least partially dismantled and reassembled in a simple manner.

This object is attained according to the invention by a surgical instrument with a main part, at least one movable part movable relative to the main part that is guided by a guide arranged on the movable part and a complementary guide arranged on the main part, a handle arranged on the main part having a stationary handle portion and an actuatable handle portion that actuates the movable part, a locking device having a first position in which the movable part is arranged in a working position and in an initial position, the locking device having a second position in which the movable part is removable at least partially from the main part, and a releasable articulated connection between the movable part and the actuatable handle portion.

A stepwise dismantling, and a mounting of the movable part to the main part to be carried out in the reverse sequence, are made possible by the constitution of the surgical instrument according to the invention. Simple and safe handling for cleaning and sterilization can thereby be provided. Furthermore, a surgical instrument can be provided which fulfills hygienic requirements. Moreover, by means of the configuration of the locking device, a surgical instrument can be provided which corresponds in handling to the prior art instruments, so that no adaptation by the operator is required. Furthermore, a simple manipulation is made possible for the at least partial removal of the movable part from the main part for cleaning. Such surgical instruments can be usable for all fields of medicine. The configuration according to the invention can be provided for all surgical instruments in which a main part and a movable part are provided and are such that they can be at least partially disassembled for cleaning.

According to an advantageous development of the invention, it is provided that the movable part and the actuatable handle are arranged at least partially pivotably and/or separably with respect to each other by means of a releasable articulated connection. Thereby, in a first phase a simple actuation of the movable part can be effected in order to remove this from the main part, according to which the movable part can be arranged by means of a guide, displaceably in the main part from an initial position into a second position, and the movable part comes free out of the guide. In a second phase, the movable part can be released from the actuatable handle due to the releasable articulated connection. A separated cleaning of the parts can thereby take place. Likewise, a simple exchange of the movable part can be made. By this constructional constitution, a simple manipulation can be provided which makes possible a rapid and simple removal of the movable part from the main part for cleaning and disinfection, and also a subsequent reassembly for surgical use.

According to an advantageous development of the invention, it is provided that the releasable articulated connection is constituted by a preferably U-shaped recess in the actuatable handle and a pin of the movable part, mounted in the recess, and that the open end of the recess is narrowed by a resiliently yieldable latch element. Thereby, after the release of the movable part from the guide of the main part, the movable part can first remain connected to the actuatable handle. After the movable part has been partially removed from the main part, for example by pivoting the movable part with respect to the main part, with a further pivoting movement the end of the movable part facing toward the stationary handle can engage on a section of the handle and can form an abutment, so that the pin mounted in the recess is moved past the yieldable latch element. Provided that the pivoting movement of the movable part is carried out near the end which receives the cutting element, due to the lever forces, small forces can be sufficient for the movable part to be completely releasable from the main part. Alternatively, it can also be provided that a removal of the movable part after it becomes free from the guide of the main part takes place such that a complete release of the movable part is given without the end of the movable main part facing toward the handle coming into contact with the abutment.

According to an advantageous development of the releasable articulated connection, it is provided that the latch element is constituted as a ball, which constricts the recess by means of a spring force which is preferably adjustable. The force for the release of the movable part from the actuatable handle can thereby be set.

According to a further alternative configuration of the releasable articulated connection, it is provided that the open end of the U-shaped recess is constituted by an elastically yieldable latch element, preferably an elastomer. A simple arrangement can thereby be provided in which a force, once preset or determined by the choice of material, makes possible the release of the pin of the movable part from the preferably U-shaped recess of the actuatable handle.

According to a further advantageous development of the invention, it is provided that when, after cleaning, the movable part is transferred into a working position, the movable part is first positioned with respect to the actuatable handle, and in a succeeding step the guide section of the movable part engages in the seating of the main part, and the guides automatically interengage by pressure on the actuatable handle. A more secure and positive assembly can thereby be attained, pressing of the actuatable handle taking place until the locking mechanism can be automatically or manually brought into the locking position, so that in connection therewith the working stroke for the movable part is released.

According to a further advantageous configuration of the invention, it is provided that the guide in the main part has a first section which runs obliquely and which moves the movable part toward the main part and changes it over into a working position. An easy bringing together and complete juxtaposition of the guide surfaces between the main part and the movable part can thereby be attained.

According to a further advantageous development of the invention, it is provided that the locking device has a latch, which can be frictionally and/or positively disposed at least in a locking position. It can be assured that during a surgical operation a self-opening of the locking device is avoided.

According to a further advantageous development of the invention, it is provided that the locking device has a latch, which is provided on the handle. A simple one-hand operation for the unlocking of the locking device can thereby be provided. The latch can be provided both on the stationary handle portion and also on the actuatable handle portion. This arrangement can be freely selected in dependence on the embodiment.

According to a further advantageous development of the invention, it is provided that a pivotable latch is provided in the stationary handle portion and engages the actuatable handle portion near a hinge pin. A compact construction can thereby be attained, being advantageously referred to the prior art geometry and size of the surgical instruments.

According to a further advantageous development of the invention, it is provided that the pivotable latch has a stop determining its locking position. The working stroke of the movable part can thereby be limited, the stroke limitation of the movable part by the latch then mostly determining the initial position of the movable part for a working stroke.

According to a further advantageous development of the invention, it is provided that the latch is pivotable into an unlocking position and releases a further pivoting region of the actuatable handle portion, which is preferably limited by a stop provided on the main part. The movable part can thereby be moved relative to the main part such that the mutually engaging guide sections can be separated from each other, in order to pivot the movable part around the articulated connection and to at least partially lift it from the main part. The size of the pivoting region can advantageously be determined in dependence on the length of the mutually engaging guides, so that even a very short pivoting region would be sufficient to separate from each other the interengaging guides between the main part and the movable part.

According to a further advantageous development of the invention, it is provided that the latch engages on a section between a pivot axis of the actuatable handle and the articulated connection. A compact construction can thereby be provided, and the latch can be integrated nearly completely into the stationary handle. Furthermore, this locking device is not troublesome for the other manipulations.

According to a further advantageous development of the invention, it is provided that the latch has a locking section which engages at a complementarily constructed pivot section of the actuatable handle. A defined arrangement of the pivot section on the locking section can thereby be given. It can advantageously be thereby attained that, by the formation of a kind of undercut or of an abutment surface and an adjoining detent cam, on returning the actuatable handle portion to its initial position after each working stroke, the latch is pressed into a locking position. Should the latch have been released even only slightly from its locking position, it is automatically brought back again into this after each working stroke. A secure manipulation can thereby be ensured. The arrangement of the latch on the stationary handle has the further advantage that a transition region which nearly completely shuts off the locking mechanism is provided between the stationary handle and the main part, so that this locking device can at the same time be protected against mechanical damage from the exterior.

BRIEF DESCRIPTION OF THE DRAWINGS

Further advantageous configurations and developments of the invention are described in detail in the further claims.

Advantageous embodiments of the invention are described in more detail with reference to the accompanying drawings.

DETAILED DESCRIPTION OF THE INVENTION

A first embodiment of a surgical instrument 11 according to the invention is shown in FIGS. 1–4. This surgical instrument 11 for example concerns a so-called punch, which is used in surgical operations for the removal of tissue, bones, or the like. The invention is not limited to these punches, but can be carried over to all surgical instruments which have the same problems regarding cleaning and sterilization and also the allocation of components.

Figure 1:
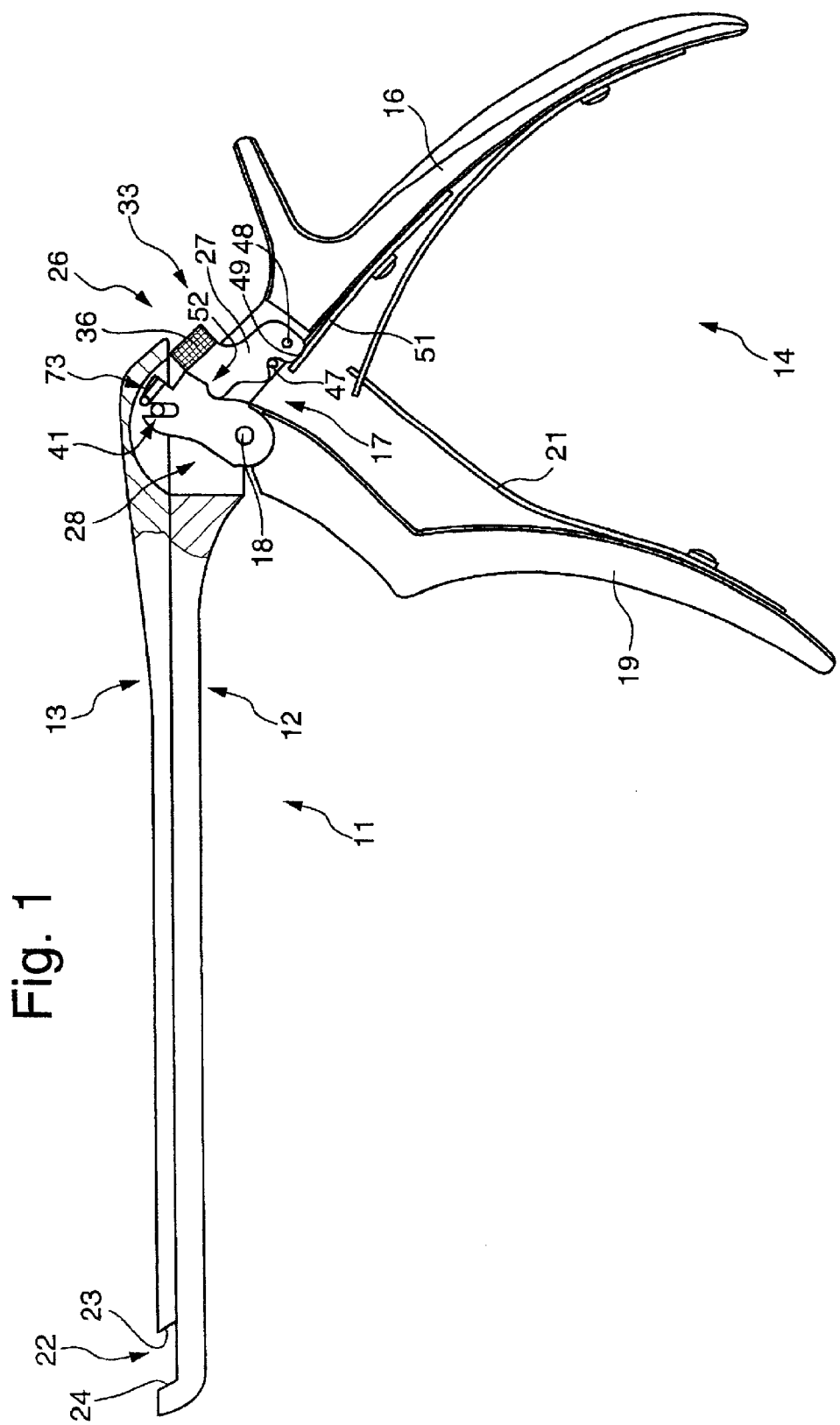
FIG. 1 shows a schematic side view of an embodiment according to the invention in an initial position.

The surgical instrument according to FIG. 1 has a main part 12 which receives a movable part 13 which is displaceable relative to the main part 12.

A handle 14 is arranged on the main part 12. The main part 12 merges into a stationary handle portion 16 of the handle 14 and has a hinge pin 18, around which an actuatable handle portion 19 is arranged to be pivotable, in the transition region 17 from the main part to the stationary handle portion 16. The actuatable handle portion 19 and stationary handle portion 16 are arranged in an initial position 22 by means of a spring 21. The cutting elements 23, 24 are spaced apart in this initial position 22, this spacing being determined by the maximum path of a working stroke. This initial position 22 is furthermore determined by a locking device 26. A latch 27 of the locking device 26 limits the pivoting movement, effected by the spring element 21, of the actuatable handle portion 19 around the hinge pin 18. A shorter lever section 28 then abuts on the latch 27.

On actuation of the handle portion 19, this is pivoted around the hinge pin 8, the movable part 13 being moved to the left in the drawing, in order to move the cutting element 23 toward the cutting element 24.

Figure 2:
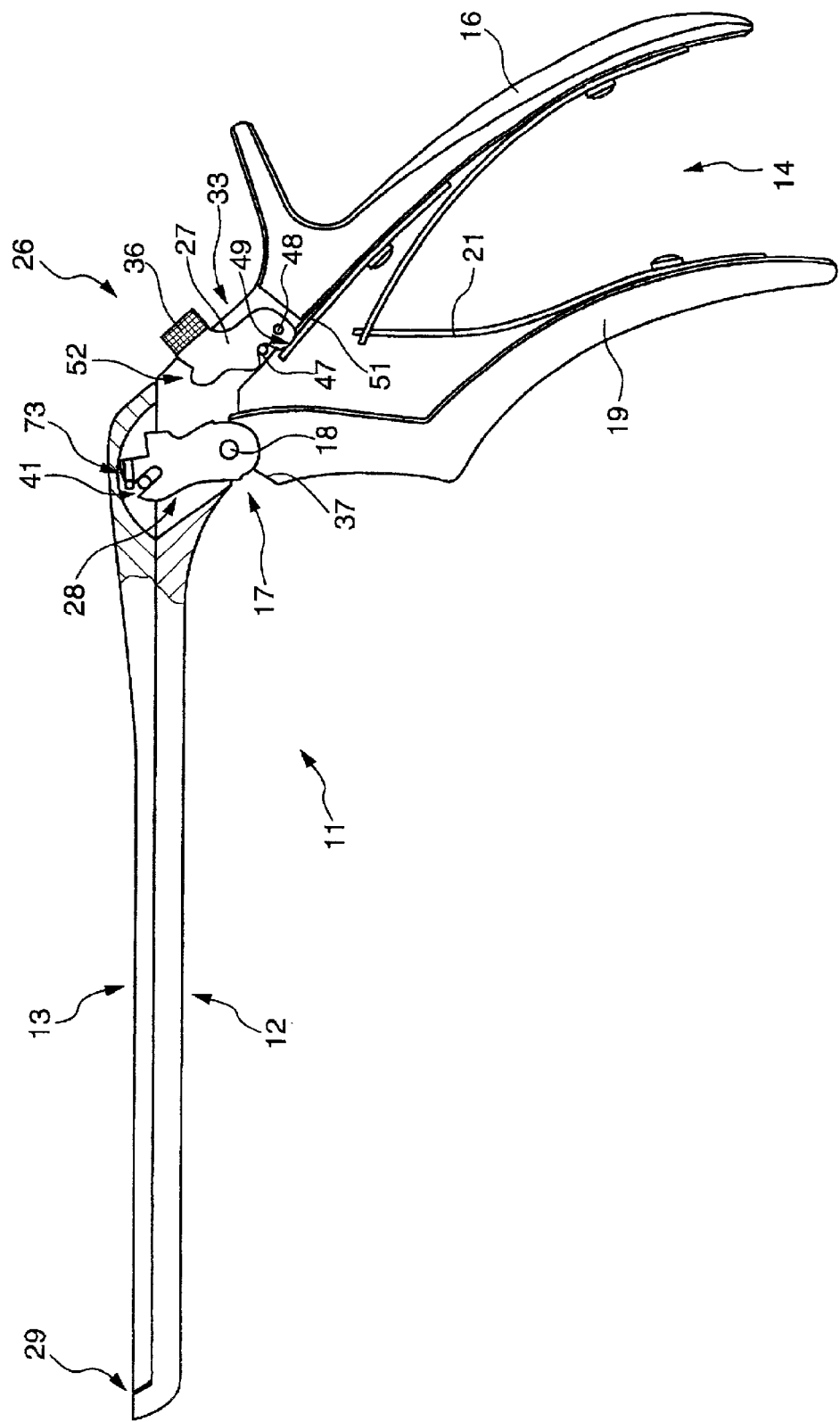
FIG. 2 shows a schematic side view of the embodiment according to FIG. 1 in a working position.

In FIG. 2, the working stroke has ended and the surgical instrument 11 is shown in a working position 29. The tissue or bone or the like to be removed is enclosed within a cavity provided within the cutting elements 23, 24, and thus can be removed. After the surgical instrument 11 has been removed from the region of the surgical operation, the handle 14 can be released, whereupon the surgical instrument 11 is automatically positioned in an initial position 22 by means of the spring element 21. The material to be removed can then be automatically released from the cutter 23, since the guide elements 31, 32 advantageously serve as an ejector.

Figure 4:
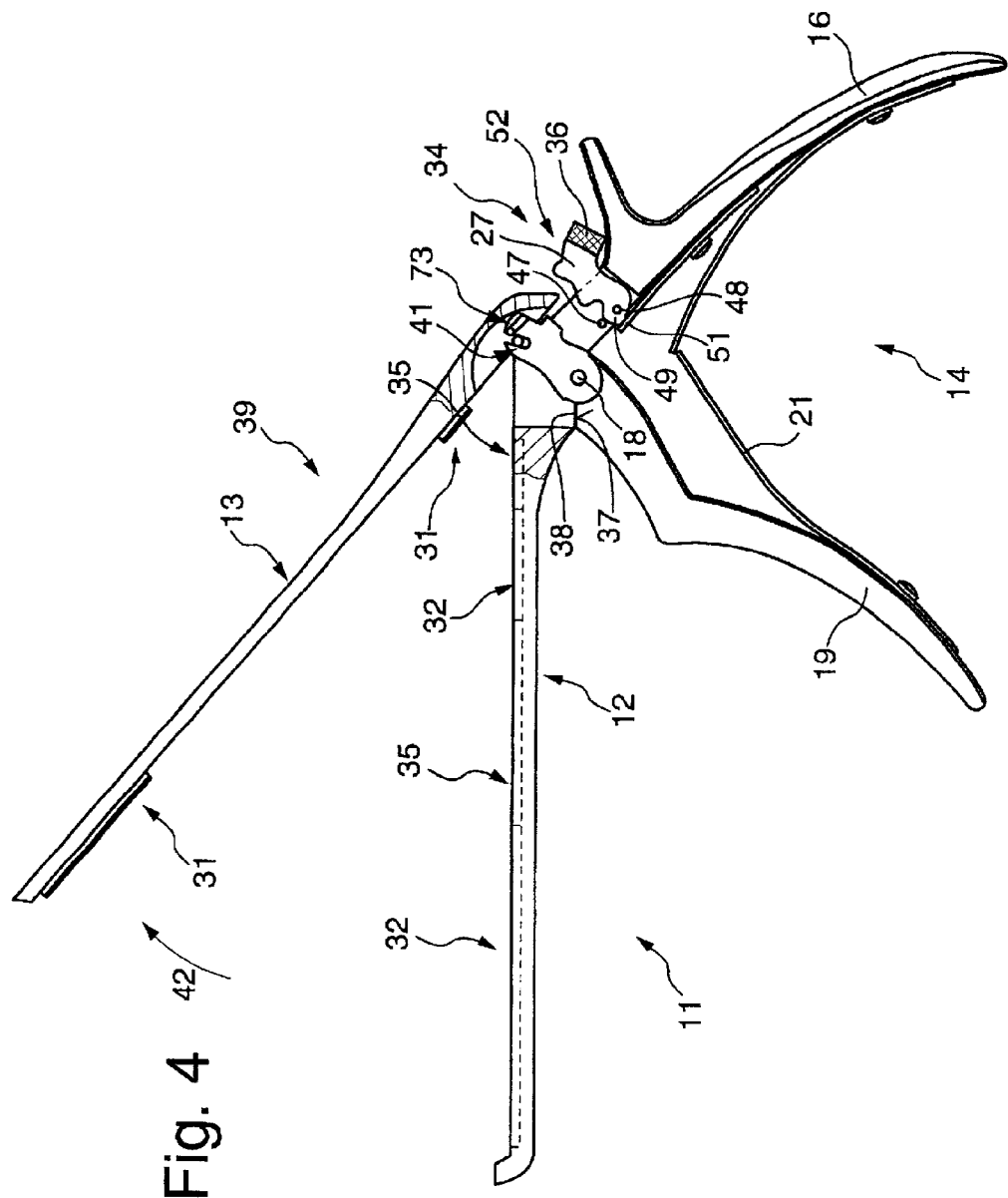
FIG. 4 shows a schematic side view of the embodiment according to FIG. 1, in a first phase.

The guide element 31 on the moving part 13 is shown as an example in FIG. 4. This spring, preferably T-shaped, engages in a corresponding groove, which forms the guide element 32, in the main part 12. The guide elements 31, 32 can also be adapted and constituted in dependence on the constitution of the surgical instrument 11.

For the cleaning and disinfection of the surgical instrument 11, it is required that the movable part 13 is at least partially lifted from the main part 12, in order to also clean and disinfect the interspaces. The locking device 26 is shown changed over from its locking position 33, as shown in FIGS. 1 and 2, into its unlocking position 34 according to FIGS. 3 to 6. According to the embodiment in FIGS. 1 to 6, this takes place by pivoting of the latch 27; advantageously, the actuatable handle 19 is moved at least partially toward the stationary handle 16, so that the latch 7 can be pivoted into the unlocking position by means of the handle portion surface 36. A further extent of path is thereby freed for the movable part 13, so that the latter is displaceable with respect to the main part 12 such that the guide elements 31, 32 are mutually released. This displacement path is limited by a stop 37 provided on the actuatable handle 19 and cooperating with a corresponding surface in the transition region 17.

The movable part 13 and the actuatable handle portion 19 are advantageously actively connected by means of an articulation 41. This articulation 41 is constituted as a pivotable articulation which at the same time makes possible a longitudinal movement of the hinge pin 18, in order to make possible an arcuate movement of the lever section 28 around the hinge pin 18 in a longitudinal movement of the movable part 13 along the main part 12.

Figure 3:
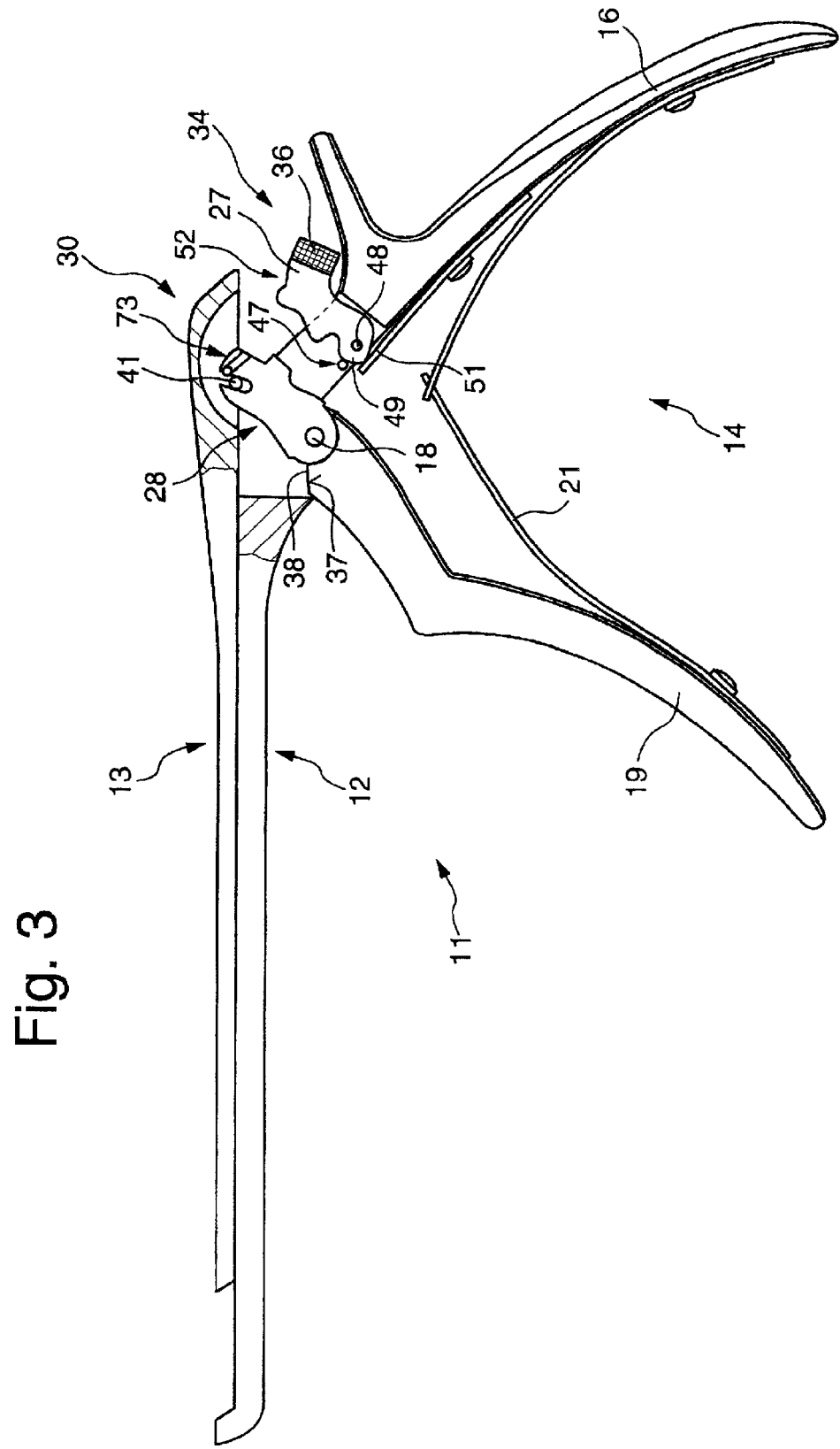
FIG. 3 shows a schematic side view of the embodiment according to FIG. 1 in an intermediate position, with unlocked locking device.
Figure 5:
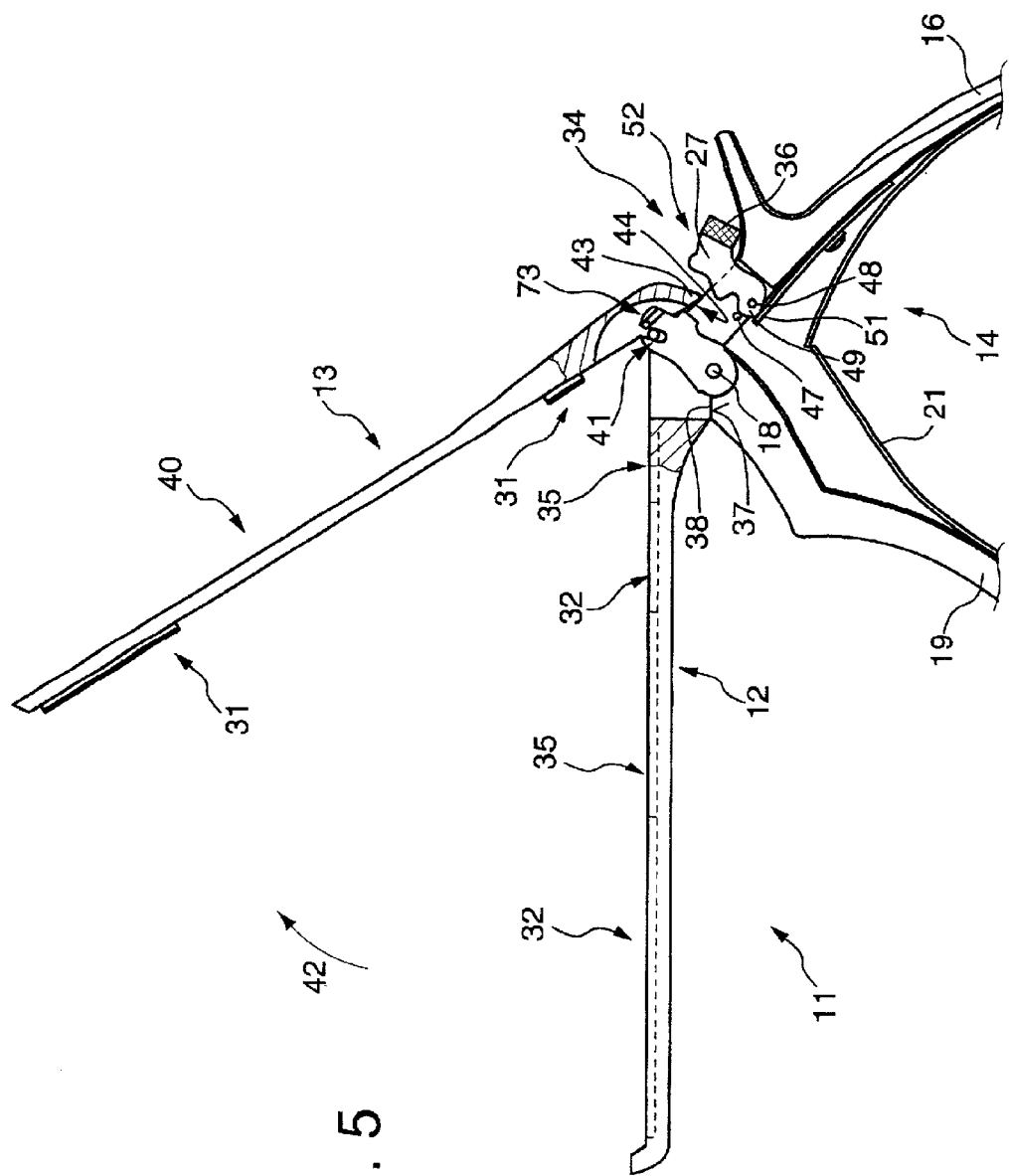
FIG. 5 shows a schematic side view of the embodiment according to FIG. 1, in the transition from the first phase into a second phase.
Figure 6:
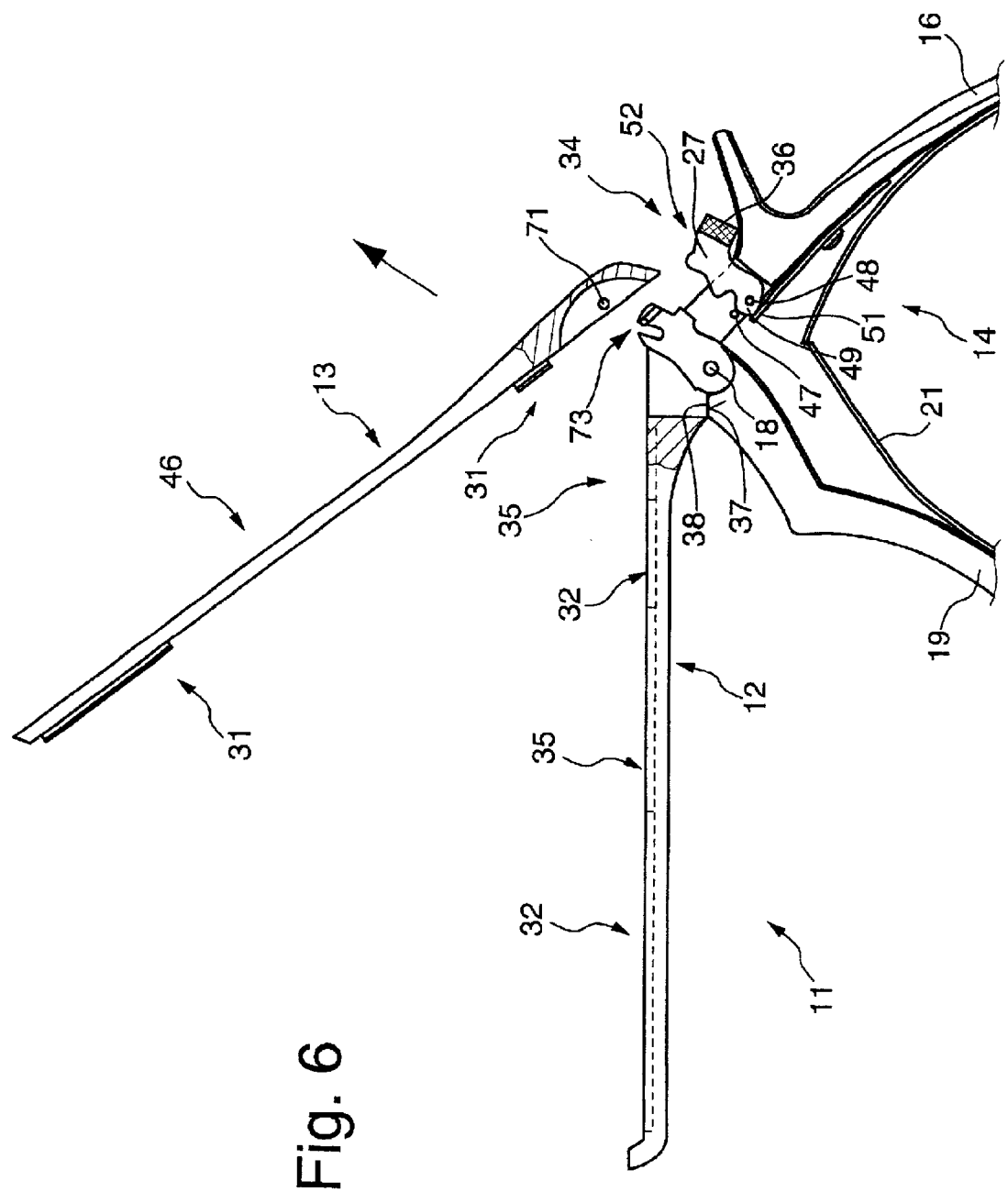
FIG. 6 shows a schematic side view of the embodiment according to FIG. 1, in which the movable part is released from the releasable articulated connection.

An intermediate position is shown in FIG. 3, and is passed through during the changing over of the surgical instrument from an initial position 22 according to FIG. 1 into a cleaning position according to FIGS. 4, 5 and 6. After the unlocking of the latch 27, the movable part 13 is transferred into the intermediate position 30 according to FIG. 3, in order to then change over into the cleaning position according to FIG. 4 by pivoting of the movable part 13 around the articulation 41. This can take place by simple actuation or pressing of the end section toward the connection 41, in order to lift up the movable part 13 from the main part 12. This arrangement has the advantage that the interspaces between the movable part 13 and the main part 12 are easily accessible and furthermore the components of the surgical element are coupled together.

In FIG. 5, the movable part 13 is shown in a second position 40, which is reached when the movable part is further pivoted around the articulated connection 41 in the direction of the arrow 42. A second phase is initiated by this pivoting, and leads to the movable part 13 being completely releasable from the main part 12, as can be seen from FIG. 6. During the continuation of the pivoting movement according to the arrow 42, an end 43 facing toward the stationary handle 16 contacts a stop 44, which is formed, for example, by a body line of the actuatable handle 16 in the transition to the supporting surface of the main part 12. This stop 44 serves as an abutment, so that a further pivoting movement according to the arrow direction 42 makes possible, due to the lever action, the facilitated release of the movable part 13 from the main part 12, as is shown in FIG. 6.

Figure 7:
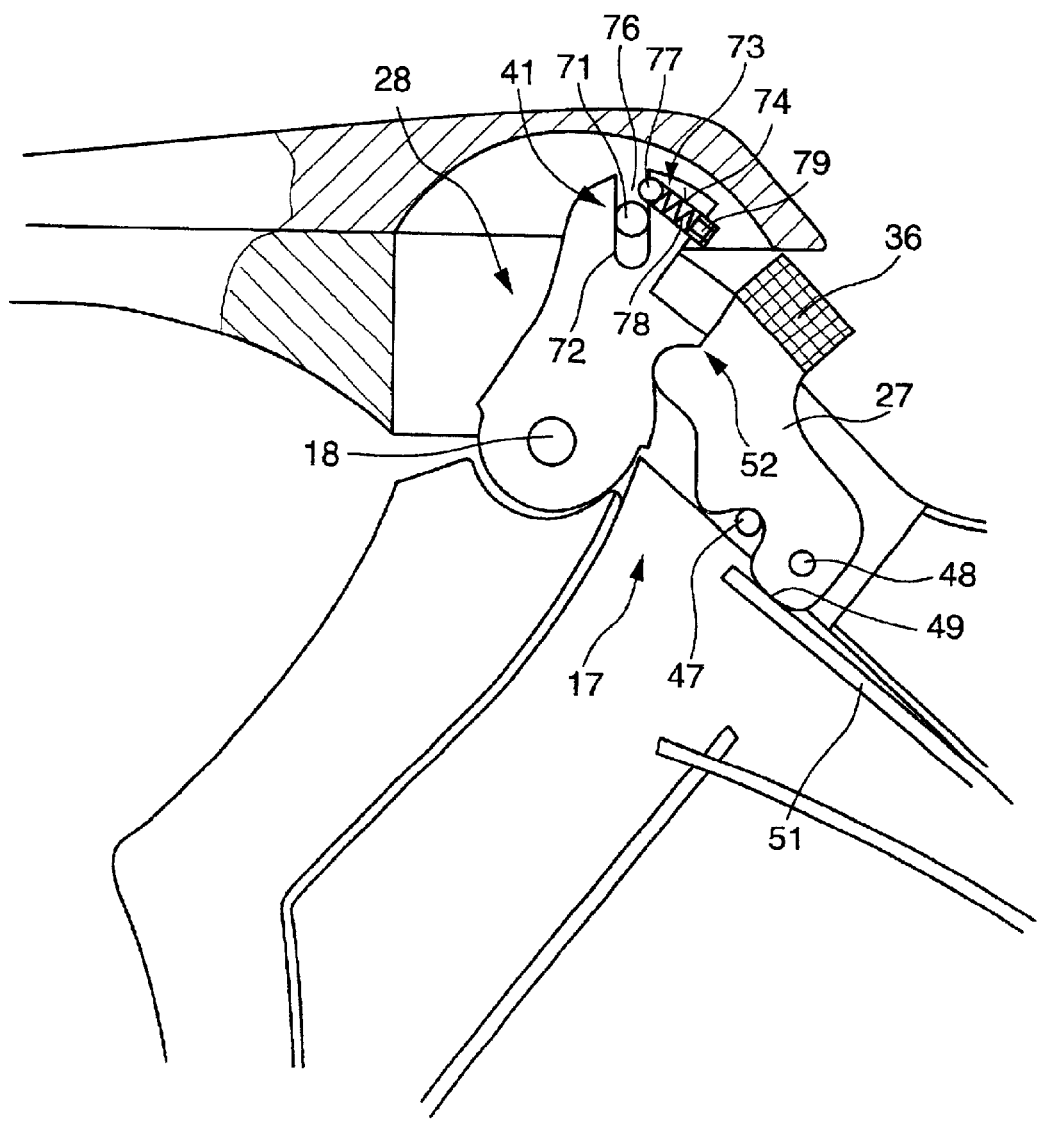
FIG. 7 shows a schematic, enlarged view of the releasable articulated connection according to the invention, of the embodiment in FIG. 1.

A first embodiment of the releasable articulated connection 41 is shown in FIG. 7. The releasable articulated connection 41 includes a pin 71 which is arranged on the movable part 13, and also a U-shaped recess 72, which is arranged in the lever section 28 of the actuatable handle 19. Furthermore, a latch element 73 is provided which on application of a force by the pin 71 is pressed back into a bore 74 of the lever section 28, so that the pin 71 can pass through the constriction 86 which is formed by the latch element 73. The latch element 73 is constituted, for example, by a resiliently yieldable latch element which has a ball 87 which is positioned in the bore 74. An opening of the bore 74, facing toward the U-shaped seating 72, is made smaller than the diameter of the ball, so that the ball cannot come out. A spring element 78 is furthermore provided in the bore 74, and is held under prestress by a threaded pin 79. By means of this threaded pin 79, the releasable articulated connection 41 can be set with respect to the force required for the release of the connection 41. Instead of the threaded section 79, a pressed-in pin can also be provided, making possible a single setting of the prestress force. Alternatively to the ball 87, further geometrical elements can also be installed which form a constriction 86 of the U-shaped seating 72 and can be pressed back into the bore 74.

The articulated connection can be released for cleaning the surgical instrument or for the exchange of the movable part 13 or of the main part 12.

An alternative configuration of the releasable articulated connection according to FIG. 7 can consist in that the constriction 86 is formed by an elastomer which is inserted, adhered, clipped, or otherwise fastened, in the region of the U-shaped recess 72. Instead of the elastomer, a plastic can also be provided which is further deformable in the elastic region and which fulfills the preconditions for the sterilization of the surgical instrument.

As a further alternative embodiment of the releasable articulated connection, it can be provided that the U-shaped recess 74 has a rigid constriction 86 and a flat is provided on the pin 71 and in a given angular position makes it possible for the pin 71 to move past the constriction 86.

A further alternative configuration of the releasable articulated connection provides that the pin of the movable part is movable transversely of the main movement direction of the movable part from a working position into an initial position and vice versa. In one position, which for example is attained by pressing the pin, the flat can be brought over into the region of the constriction, so that the pin is passed through the constriction and the movable part is removable. This position into which the pin is to be transferred by hand can be secured by a spring element so that the movable part can be separated from the main part by the active actuation of the pin.

It is advantageous for assembly that firstly the pin 71 is inserted into the recess 72, in order to subsequently change the surgical instrument 11 over into an initial position or working position 22, 23, in the sequence according to FIGS. 1 through 6.

The operation of bringing the surgical instrument 11 into readiness for use takes place in the reverse sequence. The movable part 13 is first moved toward the main part 12, with the guide element 31 engaging in a seating 35 of the main part 12, which then merges into the guide element 32. The actuatable handle portion 19 is then moved toward the stationary handle portion 16, due to which the guide element 31 engages in the guide element 32. A first section of the guide element 32 is advantageously arranged obliquely, so that the movable part, during the axial movement in the direction of the cutter 24, is simultaneously moved downward toward the main part 12, so that a nearly seamless transition between the movable part 13 and the main part 12 is provided in the initial position. The latch 27 is transferred into its locking position 33, thus abutting on a bounding element 47. The latch 27 can thereby be transferred into a defined position which at the same time determines the initial position 22, since the spring element 21 moves the actuatable handle around the hinge pin 18, due to which the lever section 28 abuts on the latch 27.

The latch 27 is arranged to be pivotable around a shaft 48. A lug 49 is provided near the shaft 48 and cooperates with a spring 51. This spring 51 on the one hand has the effect that during the actuation of the surgical instrument 11, the latch 27 is kept in its locking position 33, and also that it is held in an unlocking position 34 during cleaning. The lug 49 is accordingly constituted so that both end positions can be fixed.

The latch 27 furthermore has an abutment section 52 which is composed of a rectilinear section and a semicircular section. This configuration can be variably constituted, the function having to be fulfilled according to which, during the movement of the actuatable handle portion 19 out of the working position 29 into an initial position 22, the lever section 28 acts on the latch 27 such that the latter is moved toward the bounding element 47. It can thereby be ensured that after each working stroke the latching element, possibly being partially loosened, is guided back again into the locking position 33.

Alternatively to the embodiment according to FIGS. 1 to 7, it can be provided that the stationary handle portion 16 and the actuatable handle portion 19 are interchanged. The locking mechanism can also be arranged analogously to this. It is likewise conceivable that, instead of the latch 27 which holds the initial position 22 due to a pressure loading, this also holds due to a tensile loading, for example, when the locking element is arranged mirror-imagewise to a line which, for example, would be formed between the hinge pin 18 and the articulation 41.

It can alternatively be provided that instead of an articulated connection such as is shown in FIGS. 1–4, a U-shaped opening or the like is provided, by means of which a bolt or a pin which is arranged on the movable part 13 runs in the guide in the lever section 28 of the actuatable handle portion 19. In addition, in order to associate the movable part 13 in a captive manner with the main part 12 or with the handle 14, a further securing element, such as for example a cord, a chain, or a further bar-shaped articulated connection can be provided, in order on the one hand to be capable of being dismantled for cleaning and disinfection, and on the other hand for the movable part 13 to be associated in a captive manner with the further components of the surgical instrument.

Figure 8:
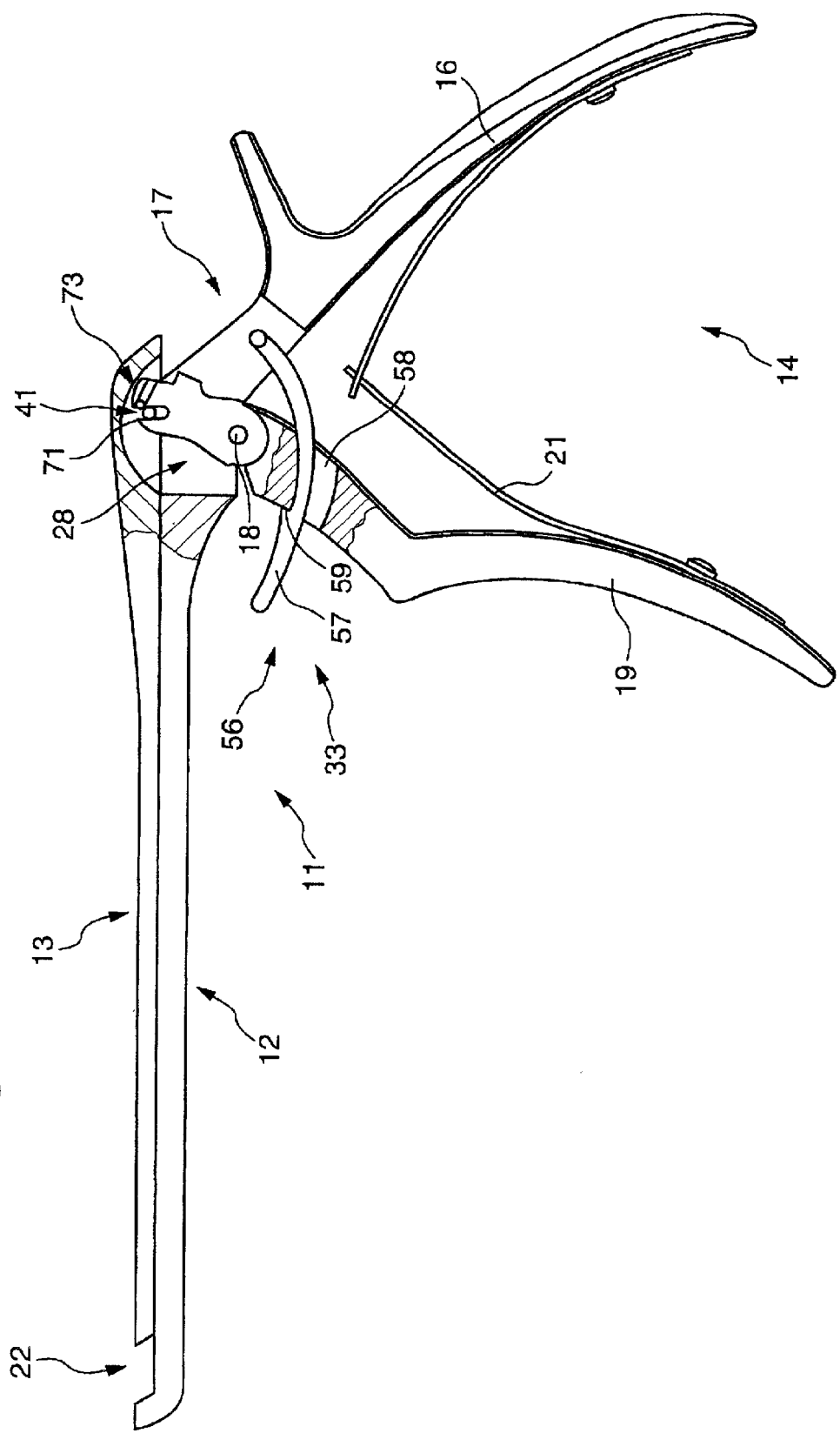
FIG. 8 shows a schematic side view of an embodiment according to the invention, with an alternative locking device.

An alternative embodiment of a locking device 56 is shown in FIG. 8. A latch 57 is arranged pivotably on the stationary handle 16 and crosses the actuatable handle portion 19. It is thereby advantageously provided that a recess 58, in which the latch 57 is guided, is provided in the handle portion 19. This latch 57 has a seating 59 by means of which the movable part 13 can be associated with the main part 12 in an initial position. This locking can be released by pressing the latch 57, so that a further pivoting region is freed for the handle portion 19 in order to change the movable part 13 over into an intermediate position 30 according to FIG. 3, to then be able to be pivoted into a position 46 according to FIGS. 4 to 6. The widened pivoting region of the handle portion 19 can on the one hand be limited by a stop 37 on a surface 38 of the main part, or by a further detent lug which is provided on the latch 57. The latch 57 is pushed or pulled by a spring, not further described, toward the hinge pin 18, and is yieldable during the actuation of the surgical instrument 11, so that the handle portion is provided pivotably toward the stationary handle portion 16.

It can alternatively be provided that the detent lug also engages on a lower section of the recess 56. In order to transfer the surgical instrument 11 from an initial position 22 into a cleaning position 46, it is required in this case that the latch 57 be moved upward.

It will be understood that this arrangement can also be provided in a mirror image fashion, both as regards the arrangement of the latch and as regards the handle portions 16, 19. This is also so for the further embodiments.

Figure 9:
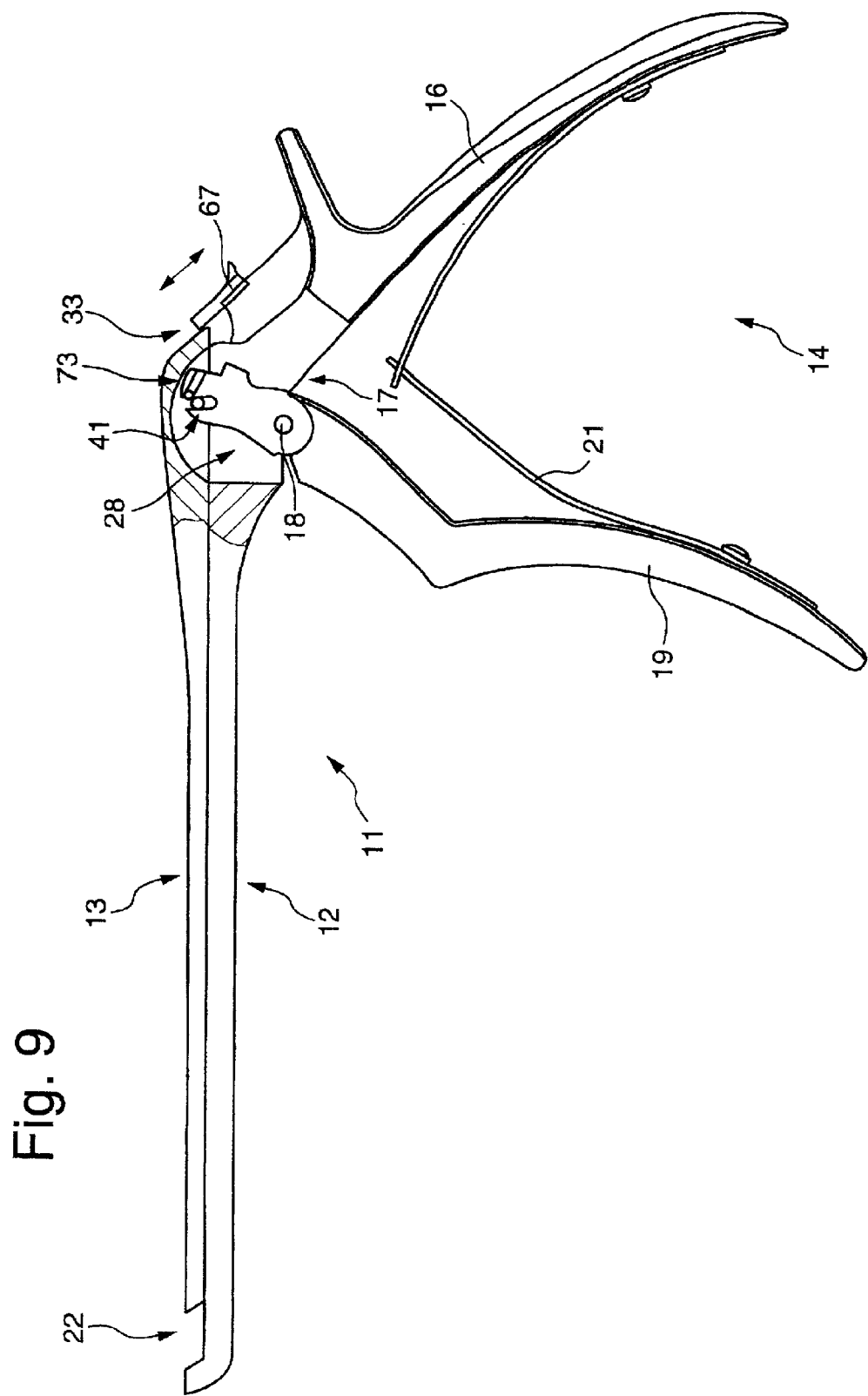
FIG. 9 shows a schematic side view of an embodiment according to the invention, with a further alternative locking device.

A further alternative locking device 66 is shown in FIG. 9. This locking device 66 has a latch 67 which engages on a rear end of the movable part 13 and limits the movement along the main part 12. The latch 67 can be transferred from a locking position 33 as shown in FIG. 6 into an unlocking position, not further shown, by means of a sliding movement toward the free end of the handle portion 16, or by a pivoting movement, which is conceivable in each direction, around a rotation axis. The movable part 13 can thereby be changed over from the working position 22 shown in FIG. 6 into the intermediate position 30 shown in FIG. 6. It can likewise be provided that the latch 67 engages, instead of a stop shown according to the drawing, even directly on the lever section 28, for example, near the articulation 41. The latch 67 can likewise be provided on the moved part 13 and can cooperate with the handle 14 or the main part 12.

Figure 10:
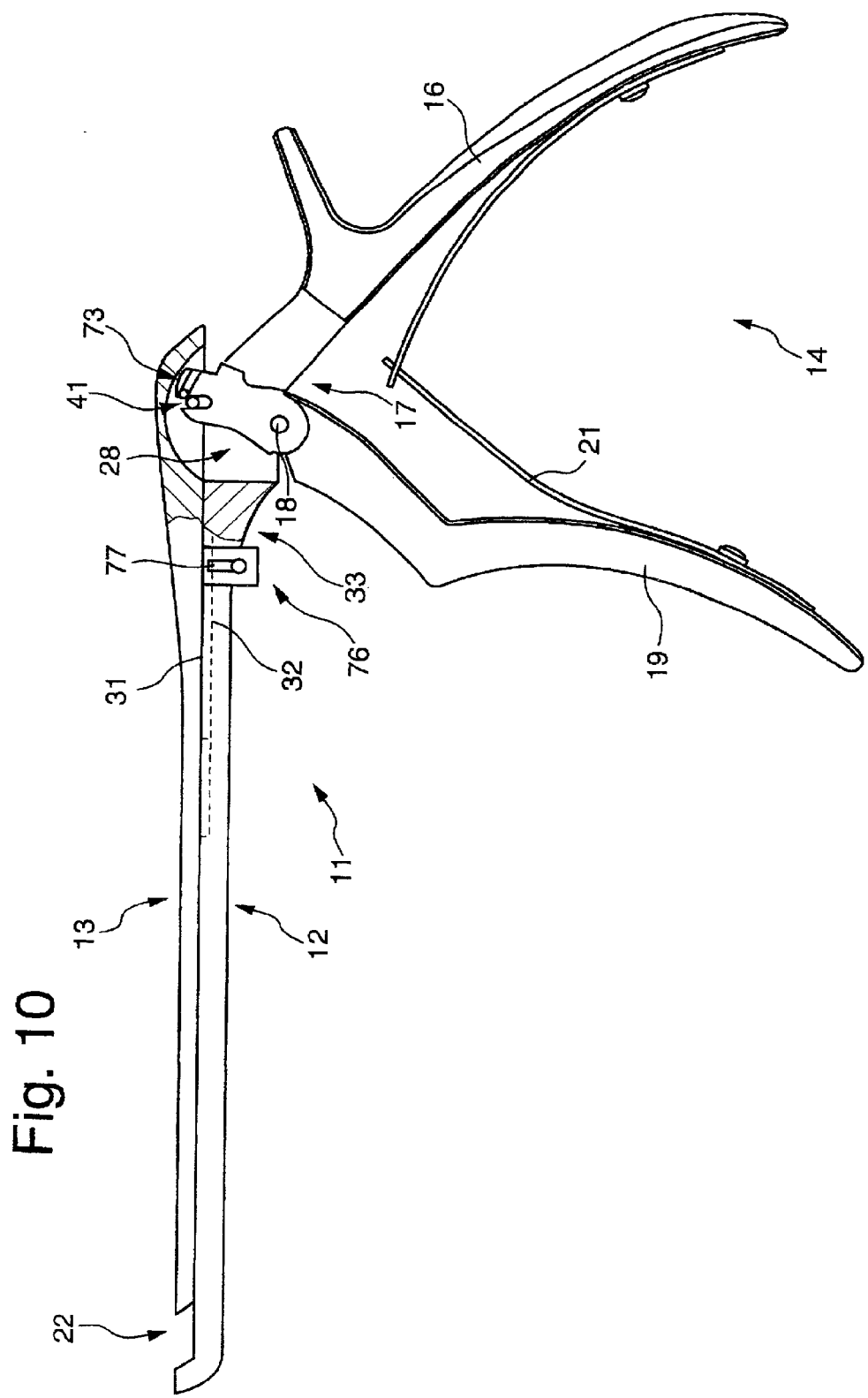
FIG. 10 shows a schematic side view of an embodiment according to the invention, with a further alternative locking device.

A further alternative embodiment of a locking device 76 is shown in FIG. 10. This locking device 76 is provided on the main part 12 and engages in the guide element 32 or a seating 35. In a locking position 33 this locking device 76 blocks, by means of a latch 77, the movement of the movable part 13 toward the right in the illustration, or into an initial position 22. The latch 77 can be actuated by pushing, pulling, sliding or folding around a rotation axis and can release the guide element 32, so that the guide element 31 can be guided out of the guide element 32.

All the embodiments have in common that the movable part 13 can be associated movably and removably with respect to the main part 12, the movable part being provided in a captive manner with respect to the main part, by means of a connection. The locking device can be provided, in dependence on the embodiment, on the stationary handle portion 16, the actuatable handle portion 19, the main part 12, or the movable part 13, and can engage in a locking position on respectively at least one adjacent part or handle portion. The locking device can be locked and unlocked by means of pulling, sliding, pressing, folding, pivoting, or the like, of a latch. It will be understood that the corresponding materials suitable for surgical instruments are used.

Alternatively to the surgical elements shown in FIGS. 1–10, which are constituted as so-called upper-cutting punches, under-cutting punches can also be provided. The cutters 23, 24 are provided on the main part 12 in a fashion mirror-image to the guide plane of the movable part 13. These embodiments can likewise be constituted according to the invention. The movable part 13 is then constituted in a stepped form, a first section in the region of the articulation 41 being retained and a section leading to the cutter 23 running on the underside of the main part 12. So that the same configuration according to the invention can be made possible and the advantages resulting therefrom can be attained, it is provided that an articulation is provided in the step-shaped transition region from the upper side to the lower side, whereby the forward step-shaped offset section can be pivoted away with respect to the main part 12 into an intermediate position according to FIG. 3, in order to be subsequently pivotable according to FIG. 4 or FIG. 5. Such modifications or supplementary measures in order to make use of the advantages according to the invention are likewise included according to the invention.

What is claimed is:

1. A surgical instrument comprising:
   a main part (12),
   at least one movable part (13) movable relative to the main part, which is guided with a guide (31) arranged on the movable part in a complementary guide (32) arranged on the main part (12),
   a handle (14) arranged on the main part (12) comprising a stationary handle portion (16) and an actuatable handle portion (19) that actuates the movable part (13),
   a locking device (26, 56, 66, 76) having a first position (33) in which the movable part (13) is arranged in a working position (29) and in an initial position (22), the locking device having a second position (34) in which the movable part (13) is removable at least partially from the main part (12) and,
   a releasable articulated connection (41) between the movable part (13) and the actuatable handle portion (19),
   wherein in a first phase the movable part (13) comes free from the guide and complementary guide (31, 32) on transfer from the initial position (22) into a further position (39), whereby the movable part (13) and the main part (12) are coupled by the releasable articulated connection (41), wherein the releasable articulated connect comprises a U-shaped seating (72) in the actuatable handle portion (19) and a pin (71) on the moveable part (13) mounted in the U-shaped seating, and
   the U-shaped seating (72) comprises an open end (76) that is constricted by a resiliently yieldable latch element (73) and in a second phase the releasable articulated connection (41) between the movable part (13) and the actuatable handle portion (19) is releasable.

2. The surgical instrument according to claim 1, wherein in a first phase after release of the guide (31) of the movable part (13) from the complementary guide (32) of the main part (12), the movable part (13) is at least partially pivotable around a pivot axis of the releasable articulated connection (41).

3. The surgical instrument according to claim 1, wherein the latch element (73) comprises a ball (87) or other construction that is arranged under a spring force in a bore (74) and forms a constriction (86) of the U-shaped seating (72).

4. The surgical instrument according to claim 1, wherein a holding force of the latch element (73) is adjustable by a threaded pin (79) arranged in the bore (74) that acts on the ball (87) by means of a spring element (78).

5. The surgical instrument according to claim 1, wherein the open end of the seating (72) comprises an elastically yieldable latch element.

6. The surgical instrument according to claim 5, wherein the elastically yieldable latch comprises an elastomer.

7. The surgical instrument according to claim 1, wherein an open end of the seating (72) comprises a rigid constriction (86), and wherein the pin (71) mounted in the seating (72) comprises a flat that in a given angular position is smaller than an inside width of the constriction (86).

8. The surgical instrument according to claim 1, wherein the open end of the seating (72) has a rigid constriction (86), and wherein the pin (71) is spring mounted transversely of an opening and closing movement of the movable part and has in a first position a diameter greater than an inside width of the constriction (86) and has in a further, actuatable position, a diameter smaller than an inside width of the constriction (86).

9. The surgical instrument according to claim 1, wherein upon changing over the movable part (13) from a cleaning position (46) to the working position (22), the guide sections (31) of the movable part engage in seatings of the main part (12), and by means of pressing the actuatable handle portion (19), the guide and the complimentary guides (31, 32) automatically engage in each other.

10. The surgical instrument according to claim 9, wherein the complementary guide (32) comprises a first section that runs obliquely in the main part (12), and which moves the movable part (13) toward the main part (12) and changes the movable guide over into the working position (29).

11. The surgical instrument according to claim 1, wherein the locking device comprises a latch (26, 56, 67, 77) which is at least one of frictionally or positively disposed at least in the first position (33).

12. The surgical instrument according to claim 1, wherein the locking device (26, 56, 66) comprises a latch (27, 57, 67) on the handle (14).

13. The surgical instrument according to claim 12, wherein the latch (27,57, 67) is provided on one of the stationary or actuatable handle portions (16, 19).

14. The surgical instrument according to claim 1, wherein the locking device comprises a pivotable latch (27) provided on the stationary handle portion (16) that engages the actuatable handle portion (19) near a hinge pin (18).

15. The surgical instrument according to claim 14, wherein the pivotable latch (27) has a bounding element (47) determining a locking position (33) of the latch.

16. The surgical instrument according to claim 11, wherein the latch (27) in an unlocking position (34) pivotably releases a further pivoting region of the actuatable handle portion (19), which is limited by a stop (37) provided on the main part (12).

17. The surgical instrument according to claim 11, wherein the latch (27) engages on a lever section (28) between the hinge pin (18) and the releasable articulated connection (41).

18. The surgical instrument according to claim 11, wherein the latch (27) comprises a locking section which engages on a complementary lever section (28) of the actuatable handle portion (19).

19. The surgical instrument according to claim 18, wherein the locking section comprises an undercut, which is formed by a bevel and a thereto adjoining detent earn.

20. The surgical instrument according to claim 1, wherein the locking device comprises a second latch (57) that engages a section of the actuatable handle portion (19) opposite a lever section (28) of the actuatable handle portion (19).

21. The surgical instrument according to claim 20, wherein the second latch (57) is guided in a recess (58) of the actuatable handle portion (19).

22. The surgical instrument according to claim 20, wherein a shoulder (59) is provided on the second latch (57) and positions the actuatable handle portion (19) in the initial position (22).

23. The surgical instrument according to claim 21, wherein by releasing the locking device between a shoulder (59) on the second latch, the second latch (57), and an edge region of the recess (58), a further pivoting region of the actuatable handle portion (19) is released and the actuatable handle portion (19) is pivotable as far as a stop (37) on the main part (12) or a further stop of the second latch (57).

24. The surgical instrument according to claim 20, wherein on changing over the actuatable handle portion (19) from a cleaning position (46) into the working position (22) an automatic locking of the second latch (57) is provided.

25. The surgical instrument according to claim 24, wherein the actuatable handle portion (19) is arranged in an initial position.

26. The surgical instrument according to claim 22, wherein the locking device comprises a third latch (67) provided on the stationary handle portion (16) that engages the movable part (13).

27. The surgical instrument according to claim 26, wherein the stationary handle portion engages at an end section of the movable part (13).

28. The surgical instrument according to claim 26, wherein the third latch (67) comprises a pivotable or displaceable latch.

29. The surgical instrument according to claim 26, wherein the third latch (67) is secured in a locking position (33).

30. The surgical instrument according to claim 29, wherein the third latch (67) in secured by means of a releasable detent connection.

31. The surgical instrument according to claim 28, wherein the locking device (76) comprises a fourth latch (77) provided on one of the main part (12) or the movable part (13).

32. The surgical instrument according to claim 31, wherein the locking device (76) is provided on the main part (12) and the fourth latch (77) engages in a guide (32) in the main part (12), in which guide the movable part (13) is guided at least sectionwise.

33. The surgical instrument according to claim 31, wherein the fourth latch (77) is provided on a region limiting the working stroke of the movable part (13).

34. The surgical instrument according to claim 32, wherein the fourth latch (77) is releasable by means of a pressing, pulling, or sliding mechanism.

* * * * *